US009332967B2

(12) United States Patent
Wu et al.

(10) Patent No.: US 9,332,967 B2
(45) Date of Patent: May 10, 2016

(54) INVERTABLE ASSAYING DEVICE WITH FLUID LEVEL ADJUSTING COVER

(75) Inventors: John Wu, San Diego, CA (US); WaiPing Ng, San Diego, CA (US)

(73) Assignee: Ameditech, Inc., San Diego, CA (US)

( * ) Notice: Subject to any disclaimer, the term of this patent is extended or adjusted under 35 U.S.C. 154(b) by 0 days.

(21) Appl. No.: 12/425,233

(22) Filed: Apr. 16, 2009

(65) Prior Publication Data
US 2010/0266449 A1  Oct. 21, 2010

(51) Int. Cl.
*G01N 33/00* (2006.01)
*A61B 10/00* (2006.01)
*B01L 3/00* (2006.01)

(52) U.S. Cl.
CPC ........... *A61B 10/0045* (2013.01); *B01L 3/5023* (2013.01); *B01L 3/50825* (2013.01); *B01L 2200/141* (2013.01); *B01L 2300/042* (2013.01); *B01L 2300/0663* (2013.01); *B01L 2300/0825* (2013.01); *B01L 2300/0858* (2013.01); *B01L 2400/0406* (2013.01)

(58) Field of Classification Search
CPC .......................... A61B 10/45; B01L 2200/141
See application file for complete search history.

(56) References Cited

U.S. PATENT DOCUMENTS

| 5,119,830 | A | | 6/1992 | Davis | |
|---|---|---|---|---|---|
| 5,403,551 | A | * | 4/1995 | Galloway et al. | ................ 422/58 |
| 5,770,458 | A | * | 6/1998 | Klimov et al. | ................ 436/518 |
| 6,277,646 | B1 | * | 8/2001 | Guirguis et al. | ............. 436/165 |
| 6,726,879 | B2 | | 4/2004 | Ng et al. | |
| 7,300,626 | B2 | | 11/2007 | Wu et al. | |
| 2003/0190745 | A1 | * | 10/2003 | Galloway et al. | .......... 435/287.2 |
| 2004/0132091 | A1 | | 7/2004 | Ramsey et al. | |

(Continued)

FOREIGN PATENT DOCUMENTS

WO 2008/061130 A2 5/2008
WO 01/89697 A2 11/2009

OTHER PUBLICATIONS (Author), ImmuTest Drug Screen Products, Ameditech, Inc. Diagnostic Product Brochure, San Diego, CA. USA.

(Continued)

*Primary Examiner* — Sam P Siefke
(74) *Attorney, Agent, or Firm* — Charmasson, Buchaca & Leach, LLP

(57) ABSTRACT

An assay test device comprises a cup container having a detachable top cover that has a volume-reducing internal structure. A pocket shaped and dimensioned to nest a chromatographic test strip cartridge is mounted against a flattened transparent portion of the cup side wall. The cartridge is held in a vertical position with an aperture near the top edge of the cup. A splash shield projects for the brim region of the cup over that aperture preventing any part of the sample fluid poured into the cup from entering the cartridge and contacting the test strips prematurely. When the lid is installed and the cup flipped upside-down, the internally projecting structure raises the level of sample fluid for better access to the cartridge aperture. The structure can be adapted to extend all the way through the inside of the cup to contact its closed bottom. A central cavity in the structure having a open end captures a small volume of fluid and preserves it for later confirmatory analysis. In one embodiment of the invention the central cavity is created by a well secured to the bottom of the cup that is telescopically engage by a cap secured to an undersurface portion of the internally projecting structure.

8 Claims, 6 Drawing Sheets

(56) References Cited

U.S. PATENT DOCUMENTS

2005/0112024 A1* 5/2005 Guo et al. .................. 422/61
2006/0029517 A1* 2/2006 Hartselle .................... 422/61
2007/0196234 A1* 8/2007 Huff .......................... 422/61

OTHER PUBLICATIONS

International Search Report, PCT Application No. PCT/US2010/031374, Ameditech, Inc.

* cited by examiner

INVERTABLE ASSAYING DEVICE WITH FLUID LEVEL ADJUSTING COVER

FIELD OF THE INVENTION

This invention relates to chromatographic reaction test devices, and more specifically to assaying devices for collecting and rapidly analyzing of fluid specimens for the presence of spurious chemicals.

BACKGROUND

The sheer volume of chromatographic immunoassay tests that today must be processed by laboratories has prompted the development of structurally simple, inexpensive and thus disposable test devices of the type disclosed in U.S. Pat. No. 5,403,551 Galloway et al, U.S. Pat. No. 5,770,458 Klimov et al., U.S. Pat. No. 6,726,879 Ng et al., and U.S. Pat. No. 7,300,626 Wu et al.

These tests typically include a number of chromatographic test strips held in one or more pockets where they subjectable to contact the fluid specimen collected. Devices such as the IMMUTEST brand cartridge commercially available from Ameditech, Inc. of San Diego, Calif. can be dipped into a container holding a fluid specimen, or the specimen can be deposited on the strips using a pipette or similar device in order to initiate test process.

In some devices such as the so called "no-step"-type devices, the test is initiated immediately by the act of depositing fluid into the cup. However, it is preferable in some situations that the test be initiated by a skilled technician who can promptly read the results. This may not occur when the specimen donor deposits fluid into the cup. Devices such as U.S. Pat. No. 7,300,626 Wu, et al. allow for initiation of the test by changing the orientation of the cup.

An additional problem with fluid specimen cup devices occurs when too little fluid is supplied such that contact cannot be made reliably with the strips.

It can be useful to store a subset of the fluid sample provided for later use in confirmatory testing in the lab as disclosed in U.S. Pat. No. 6,726,879, Wu, et al.

The instant invention results from attempts to expedite the assay process by reducing the amount of user's manipulation of the testing device, reduce the volume of sampling fluid needed, minimize the risk of misinterpretation of the results, and further reducing the device manufacturing cost and yet offer added versatility of use.

SUMMARY

The principal and secondary objects of the invention are to provide an improved fluid specimen test device.

These and other objects are achieved by an cup wherein testing can be initiated by reorientation of the cup and which uses a volume reducing structure to allow for specimens of reduced volume.

In some embodiments there is provided an assaying device for collecting and analyzing a fluid specimen for detection of spurious chemicals consist of a cup having its open top detachably closed by a circular lid. In some embodiments a common cartridge of chromatographic test strips is nested in a pocket formed in a flattened and windowed portion of the cup wall. In some embodiments the cartridge is preferably oriented to admit the sample fluid from an aperture in its upper region. In some embodiments a detachable splash shield extending from an area near the brim of the cup over the top pocket opening prevents the fluid sample poured into the cup from entering the cartridge and directs it toward the bottom center of the cup. In some embodiments the shield acts as a barrier that keeps the cartridge locked into the pocket. In some embodiments a structure in the form of a conical depression of the lid top portion project deeply into the cup, substantially reducing its volumetric capacity. In some embodiments, after the sample has been introduced into the cup, and the lid hermetically closed, the cup is flipped upside-down to bring part of the sample in contact with the cartridge aperture and consequently the testing strips. In some embodiments the conical depression helps the access of the sample to the cartridge by increasing the level of fluid specimen in the lower peripheral region of the inverted cup.

In some embodiments a small tubular enclosure having an open lower end extends from the undersurface of the depressed lid all the way to the bottom of the cup where end opening is hermetically sealed by a compressibly resilient pad or ring of elastomeric material. In some embodiments, as the lid is secured over the top of the cup, the tubular enclosure automatically captures a small amount of fluid specimen that may be preserved for a later time control analysis.

In some embodiments there is provided an assaying device for collecting a sample, analyzing a first portion and preserving an unadulterated second portion, said device comprises: a container having an inner chamber, a central vertical axis, an open top, peripheral wall and a closed bottom; said peripheral wall including a flat section having a transparent window; a pocket shaped and dimensioned to hold a cartridge of chromatographic assay strip within said chamber and against said window; a cover shaped and dimensioned to hermetically seal said open top; and including a structure projecting downwardly into said chamber when said cover is placed over said top.

In some embodiments the device further comprises a tubular enclosure extending downwardly from an undersurface portion of said cover and having a bottom opening positioned to come in closing contact with a structure associated with said closed bottom when said cover is placed over said top.

In some embodiments the device further comprises a splash shield extending from said wall over an upper section of said pocket.

In some embodiments the device further comprises one of said cartridge including an upper portion having an aperture for admitting fluid sample.

In some embodiments the shield is detachably secured to said wall in a position to locking said cartridge into said pocket.

In some embodiments the pocket and the cartridge are further shaped and dimensioned to allow for mounting said cartridge in an upright orientation or an inverted orientation with respect to said container.

In some embodiments the device further comprises a resiliently compressible pad hermetically sealing said bottom opening against said closed bottom when said cover is placed over said top.

In some embodiments the structure comprises a depression in said cover. In some embodiments said depression is axially symmetric about a rotation axis of said cover. In some embodiments the depression is funnel-shaped.

In some embodiments the tubular enclosure is axially aligned with the major cylindrical axis of the cup.

In some embodiments the cover comprises a horizontal surface and a peripheral circular flange shaped and dimensioned to intimately lock over an upper wall section of said container.

In some embodiments the depression has a central cavity closed at a upper region, and extends to contact said closed bottom when said cover is secured over said top.

In some embodiments the device further comprises means for releasably hermetically sealing said cavity against said bottom structure.

In some embodiments, it is provided that in a assay cup having a sealable top cover wherein a test strip is held in a peripheral region of the cup wall, an improvement which comprises a volumetric capacity-reducing body extending from said cover into said cup.

In some embodiments the body extends into contact with a structure associated with a closed bottom area of said cup; and has a central cavity open at a lower end, said cavity being sized to capture a small volume of fluid sample when said top cover is placer over said cup.

In some embodiments the improvement further comprises a cartridge holding said strip and having an aperture in a upper region of said cup.

In some embodiments the improvement further comprises a shield projecting from a internal wall area of said cup over said aperture.

In some embodiments the device comprises a sealable tubular enclosure having a lower portion secured to said bottom and an upper portion secured to an undersurface portion of said structure and being shaped and dimensioned to telescopically engage said upper portion when said cover is placed upon said container. In some embodiments one of said lower and upper portions comprises a surface formed to have a pit.

DESCRIPTION OF THE EXEMPLARY EMBODIMENTS OF THE INVENTION

Figure 1:
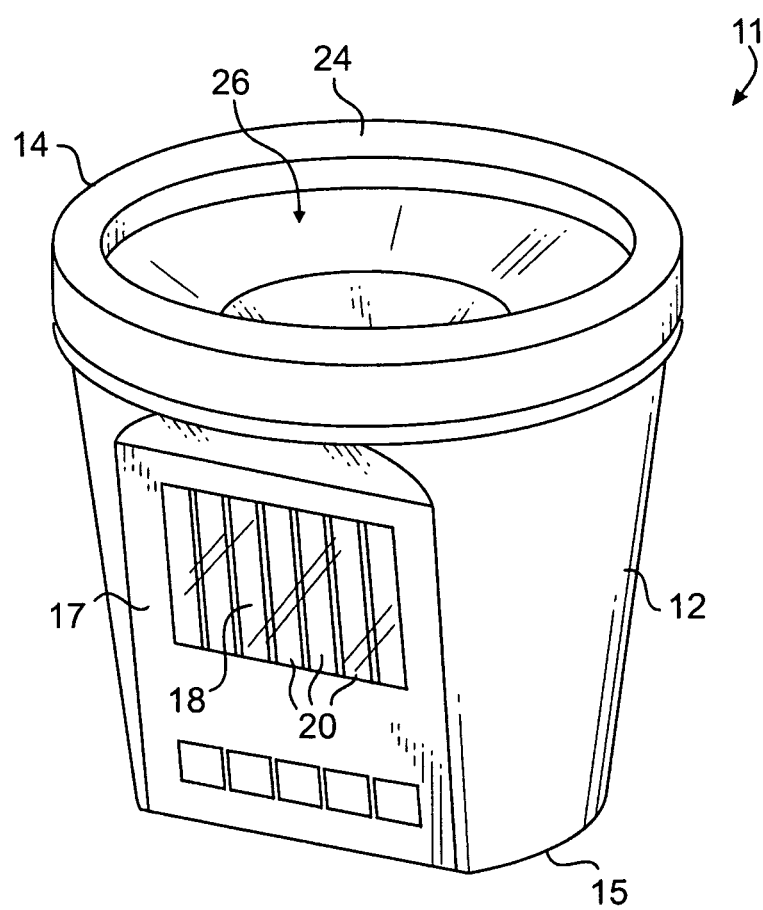
FIG. 1 is a diagrammatic perspective view of a testing cup according to the invention.
Figure 2:
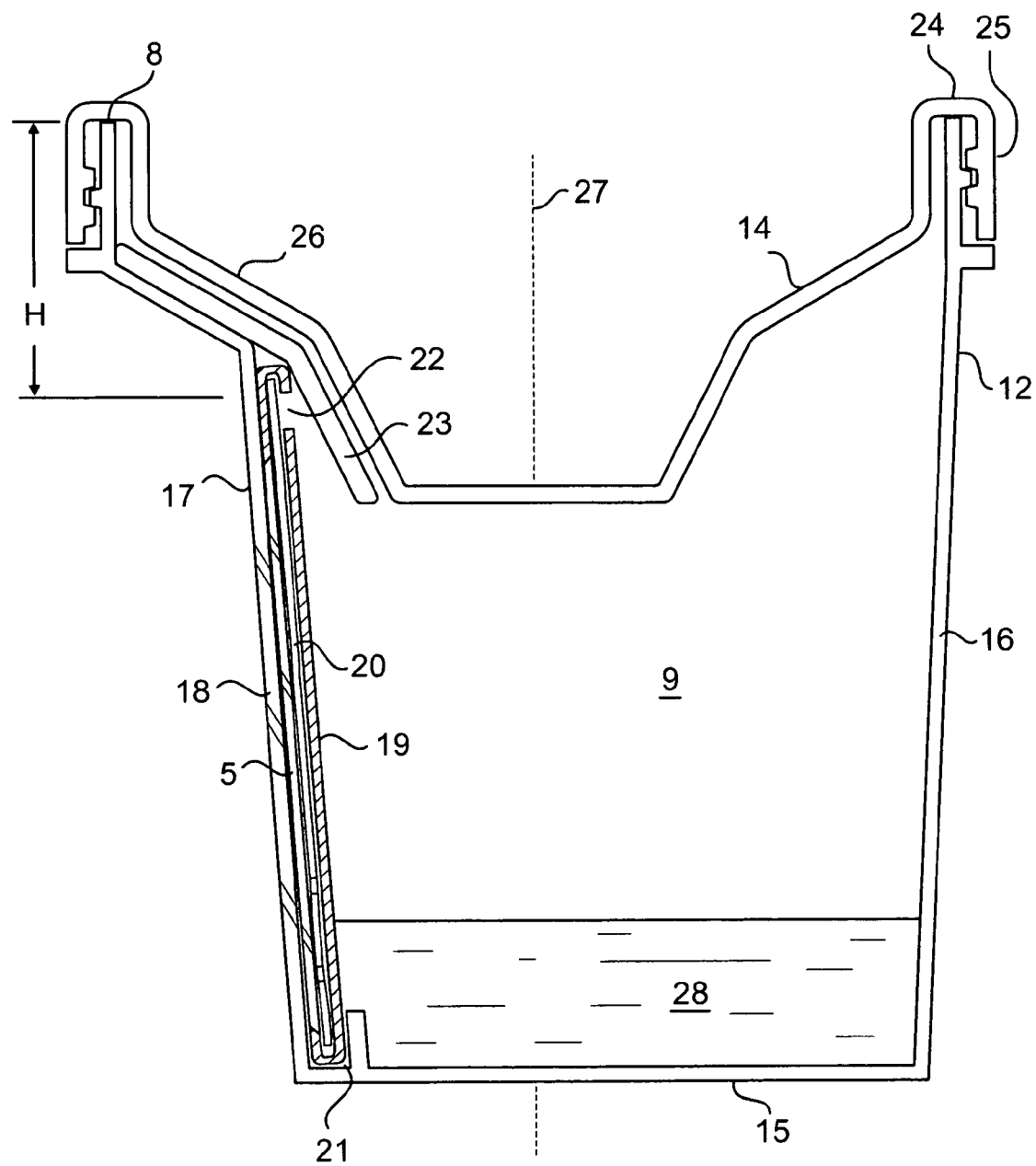
FIG. 2 is a diagrammatic cross-sectional view thereof in an upright pre-test position.
Figure 3:
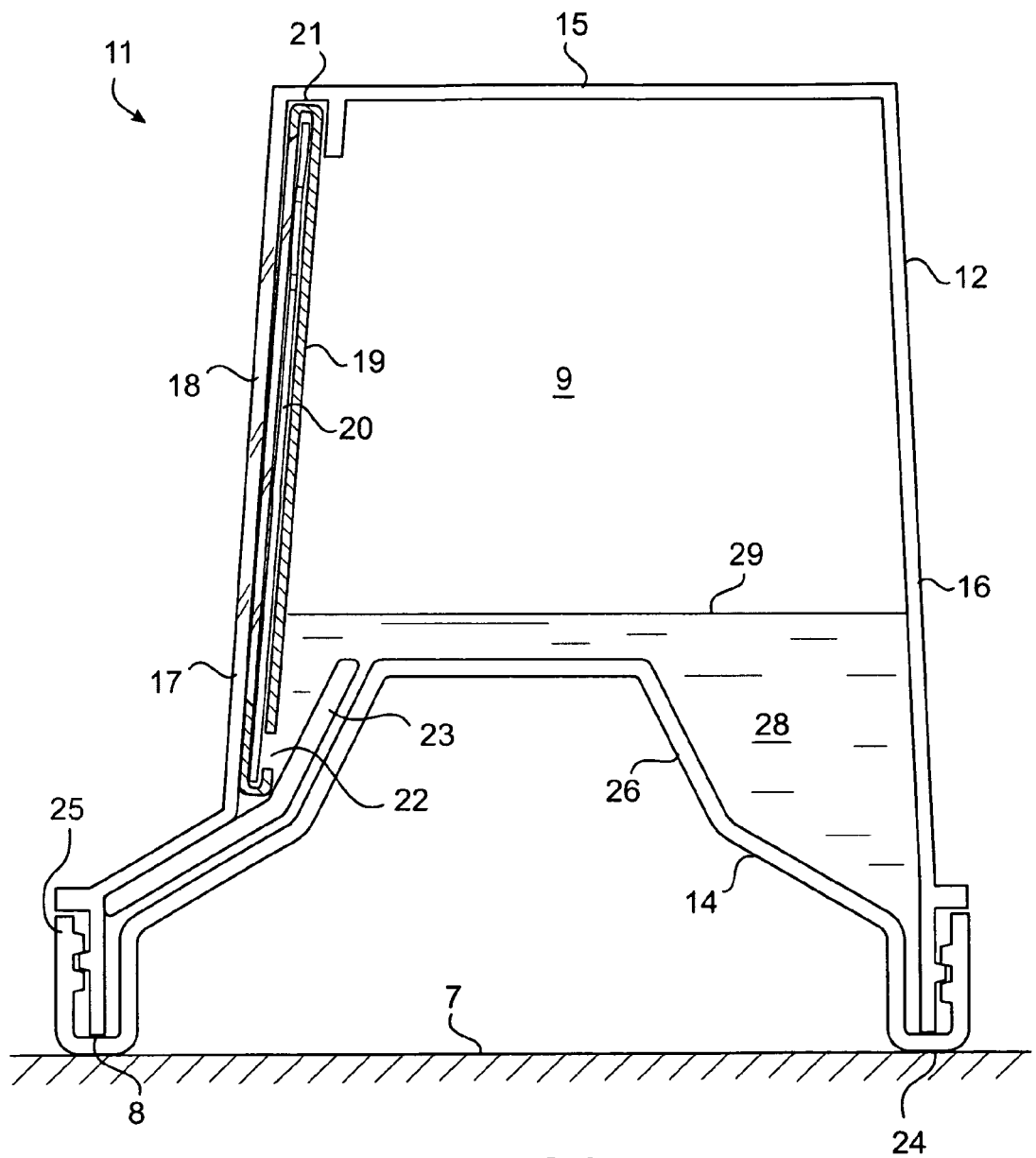
FIG. 3 is the diagrammatic cross-sectional view in an inverted testing position.

Referring now to the drawing, there is shown in FIGS. 1-3 an assaying device 11 including a container cup 12 having an open top closed by a circular cover or lid 14, a closed bottom 15 and slanted peripheral wall 16 enclosing an internal chamber 9. A flattened section 17 of the peripheral wall forms a transparent window 18 through which is viewed a cartridge 19 mounting a number of chromatographic test strips 20 behind a transparent panel 5.

The cartridge is held in a pocket 21 formed against an inner surface of the flattened section 17. The cartridge has an aperture 22 accessible in the upper part of the pocket 21 and spaced a distance H from the open top of the cup. A splash shield 23 is detachably secured below the brim 8 of the cup and extends over the upper section of the pocket and the cartridge aperture. The shield prevents any part of a fluid specimen being poured into the cup from prematurely reaching the exposed part of the test strip exposed by the aperture 22 an inadvertently initiating the test. The shield can also act as a barrier to prevent the cartridge from slipping out of the pocket 21. The shield can be glued, welded or snapped into place after the cartridge has been placed in the pocket.

The shape and dimensions of the pocket can be selected to accommodate commercially available-type cartridges such as the IMMUTEST brand cartridge commercially available from Ameditech, Inc. of San Diego, Calif., thus decreasing manufacturing costs. The shape and dimensions of the pocket can be further selected to allow such a cartridges to be held in the preferred inverted orientation as shown, or optionally in an upright orientation where the aperture is located near the cup bottom.

The cover 14 comprises a generally flat horizontal surface portion 24 and a threaded peripheral circular flange 25. A generally conical or funnel-shaped depression 26 in the center of the cover forms a substantially conical void which extends into the chamber 9 below the cartridge aperture so that the volume of the chamber is reduced. In this way, the conical depression acts as a volume reducing structure which helps in the access of the sample to the cartridge by increasing the level 29 of fluid specimen in the lower peripheral region of the inverted cup as shown in FIG. 3. This allows for a smaller amount of fluid to be used. It is important to note that the depression is selected to be symmetric about the rotation axis 27 of the cover so that it does not interfere with the splash shield 23 while the cover is being twisted into place.

As illustrated in FIG. 2, after a fluid specimen 28 has been poured into the cup and the cover has been installed, the specimen does not reach the aperture 22 leading to the test strips until the cup is flipped upside-down as shown in FIG. 3. The generally flat horizontal surface portion 24 of the cup provides stable support for the cup in the inverted orientation when placed on a substantially flat horizontal surface 7.

Figure 4:
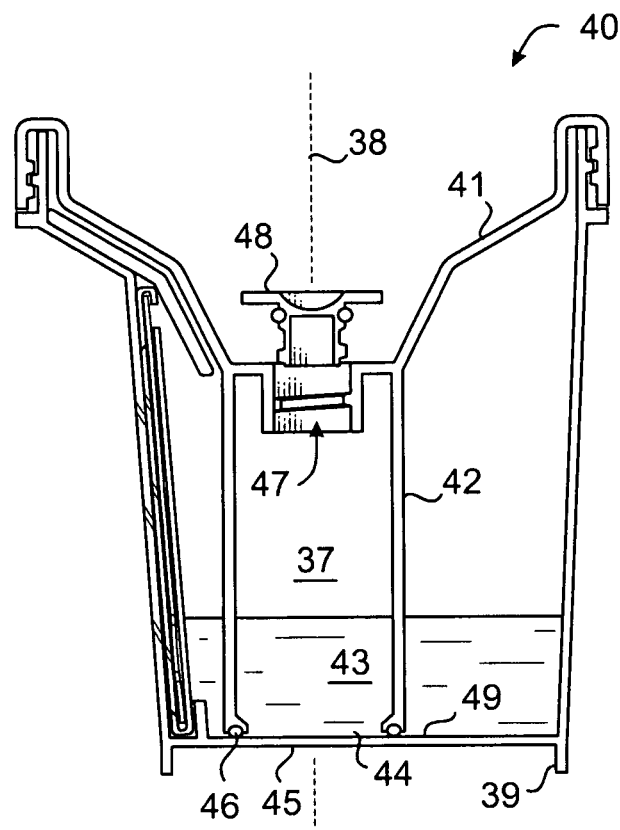
FIG. 4 is a diagrammatic partially exploded cross-sectional view of an alternate embodiment of a testing cup having a confirmation sample preserving feature.

Referring now to FIG. 4 there is shown an alternate embodiment of a testing device 40 which has a cover 41 which is prolonged by a tubular central enclosure 42 having an internal cavity 37 for trapping a separate aliquot, or small volume 43 of the fluid sample for later confirmatory testing. The enclosure has an open bottom 44 that extends all the way to the upper surface of the closed bottom 45 of the cup. A ring or pad 46 of a resiliently compressible elastomeric material hermetically seals the enclosure 42 when the cover is tightly screwed upon the cup. An access port 47 closed by a releasable plug 48 is provided in the top of the enclosure.

A small volume 43 of fluid can be captured within enclosure 42. That volume can be accessed for subsequent controlled confirmation testing through the unplugged access port 47. That access port may conveniently be kept unplugged during installation of the cover to allow air to escape and thus ease entry of the fluid into the enclosure 42, then resealed before further handling or inverting the cup. The releasable plug is shown to have a threaded engagement with the port and a circumferential O-ring to provide an hermetic seal. Additionally, care should be taken to ensure that the upper surface 49 of the closed bottom 45 remain adequately flat under the stress of the engaging pad so that a rugged seal is made. To improve stiffness of the closed bottom, a peripheral flange 39 or other stiffening structures can be provided. The bottom surface is a structure associated with the cup bottom.

It should be noted that the internal dimensions of the central enclosure can be selected to trap an adequate amount of fluid for the small volume. Further, the outer dimensions of the central enclosure can be selected to help determine the amount of volume reducing capability of the enclosure. In other words, the shape and dimension of the central enclosure can be selected to allow the central enclosure to act as the volume reducing structure for the chamber of the cup. Because a subset of the sample is trapped for later confirmatory testing, the volume provided to the cartridge is reduced. Therefore, use of the volume reducing depression is preferred in all of the exemplary embodiments.

Figure 5:
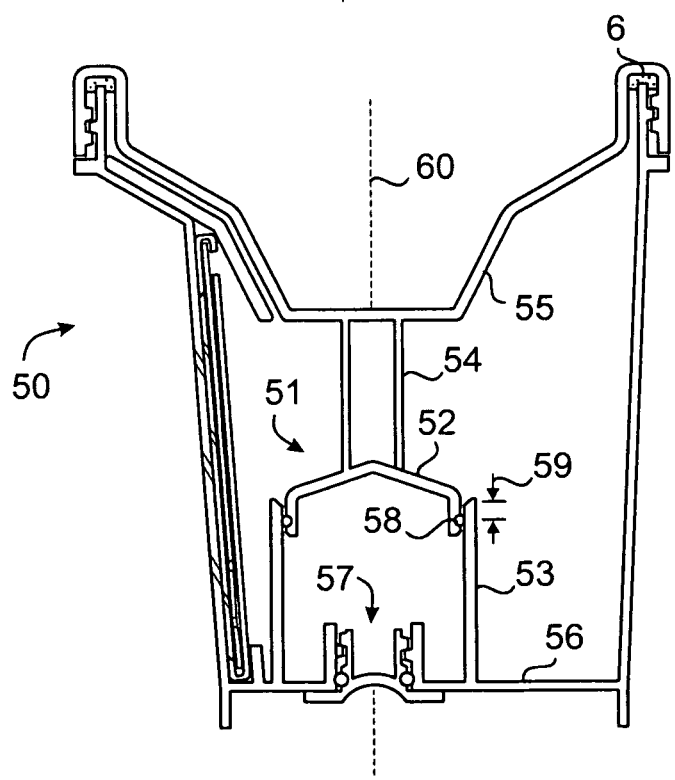
FIG. 5 is a diagrammatic cross-sectional view of an alternate embodiment of a testing cup having an alternate confirmation sample preserving feature having an enhanced low volume dispensing capability.

In the alternate embodiment of the assay device 50 illustrated in FIG. 5, the tubular enclosure 51 consists of two telescoping portions, namely, a plunger cap 52 associated with the cover and a well 53 associated with the cup bottom. The plunger cap is supported by a shank 54 projecting from the undersurface of the conical depression 55. The well 53 is bonded to the bottom 56 of the cup and has a releasably plugged access port 57 through the bottom. The cap telescopingly engages the well to seal off the enclosure and thus trap a small volume of sample for later confirmatory testing. An O-ring 58 surrounding the plunger further guarantees the sealing of the tubular enclosure 51. The telescoping nature of the O-ring engagement between the plunger and well allows for an hermetic seal even when inconsistencies occur in manufacturing tolerances. The distance 59 of telescoping penetration is minimized to avoid the necessity of allowing air to escape during engagement. This embodiment also provides a washer 6 nested within the thread flange of the cover and made from resilient material can enhance hermeticity of the seal between the cover and the cup.

It should be noted that in the embodiment of FIG. 5, the tubular enclosure 51 is centrally aligned with the central vertical axis 60 of the cup to allow for automatic alignment of the cap 52 and well 53 as the cover is being installed upon the cup. In the embodiment of FIG. 4 although the location of the enclosure 42 is shown to be in coaxial alignment with the central vertical axis 38 of the cup, it should be clear that coaxial alignment is not necessary so long as the upper surface of the cup is substantially flat or other steps are taken to achieve hermetic sealing of the enclosure.

Figure 6:
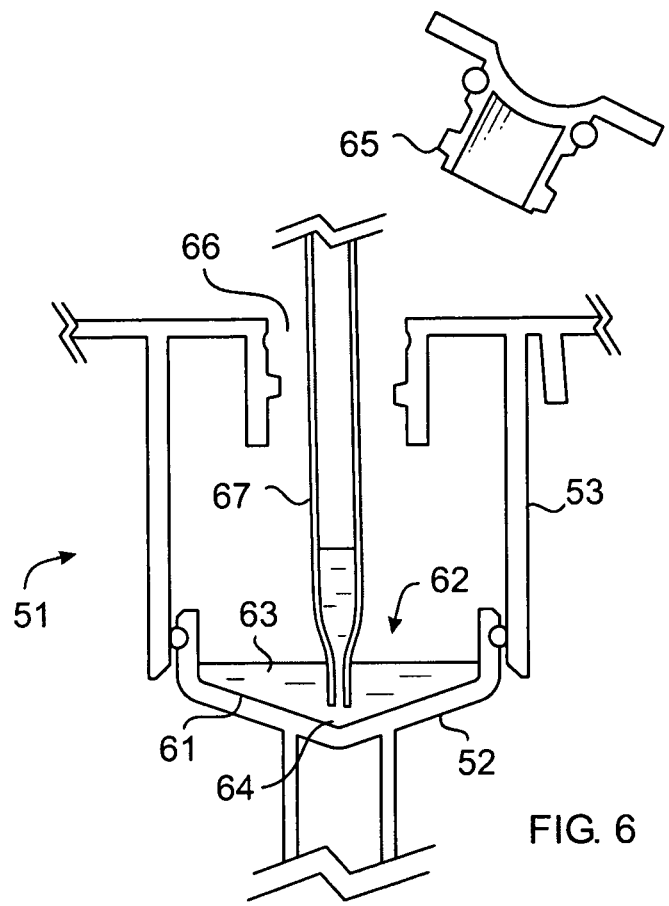
FIG. 6 is a diagrammatic partially exploded cross-sectional view of the confirmation sample enclosure of the embodiment of FIG. 5 in an inverted orientation.

Referring now to FIG. 6, there is shown a close-up view of the tubular enclosure 51 of the device of FIG. 5 shown in an inverted orientation. The inner surface 61 of plunger cap 52 is shaped to form a substantially conical receptacle 62 so that when the enclosure is in an inverted orientation, an aliquot of fluid forms a pool 63 within the receptacle where the apical portion of the conical receptacle forms a pit 64 in the deepest region of the pool. In this way, once the plug 65 has been removed from the access port 66, a pipette 67 or other fluid removing apparatus can be inserted into the pit to remove the maximum amount of fluid as the remainder collects in the pit.

Figure 7:
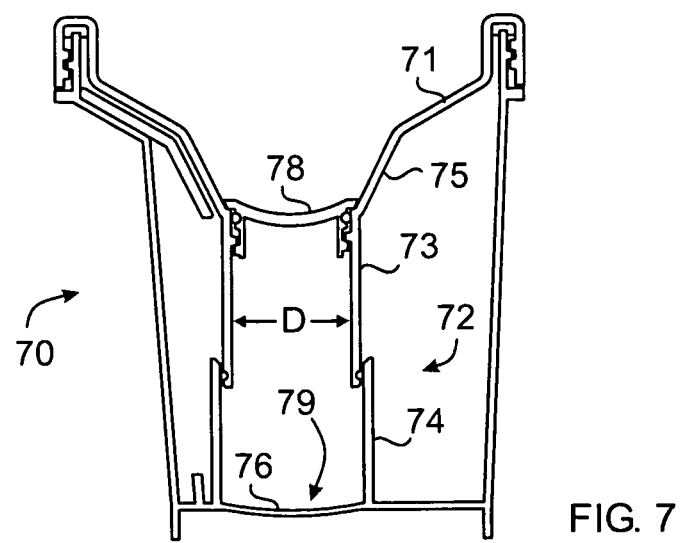
FIG. 7 is a diagrammatic cross-sectional view of an alternate embodiment of a testing cup having a confirmation sample preserving feature having enhanced pouring capability.

In the alternate embodiment of the assay device 70 illustrated in FIG. 7, the tubular enclosure 72 includes two telescoping portions, namely, a plunger cap 73 and a well 74 similar to the embodiment of FIG. 5. However, in this embodiment the plunger cap 73 is an elongated tubular structure extending from the undersurface of the conical depression 75 of the cover 71, and provides an access port closed by a releasable plug 78 in the top of the enclosure similar to the embodiment of FIG. 4. The port and plug have been widened to substantially span the diameter D of the receptacle 74 formed by the internal surface of the plunger cap. In this way, substantially all of the fluid trapped within the enclosure 72 can be easily poured out of the open access port, unlike in the embodiment of FIG. 4 when a small amount of fluid can become trapped in the circumferential region of the cavity surrounding the access port 47. In the present embodiment, the bottom surface 76 of well 74 is shaped to form a substantially semispherical concave receptacle 79 so that remaining fluid collects within the pit formed in the deepest portion of the receptacle. In this way, once the plug has been removed from the access port, a pipette or other fluid removing apparatus can be inserted and remove the maximum amount of fluid from the receptacle.

Figure 8:
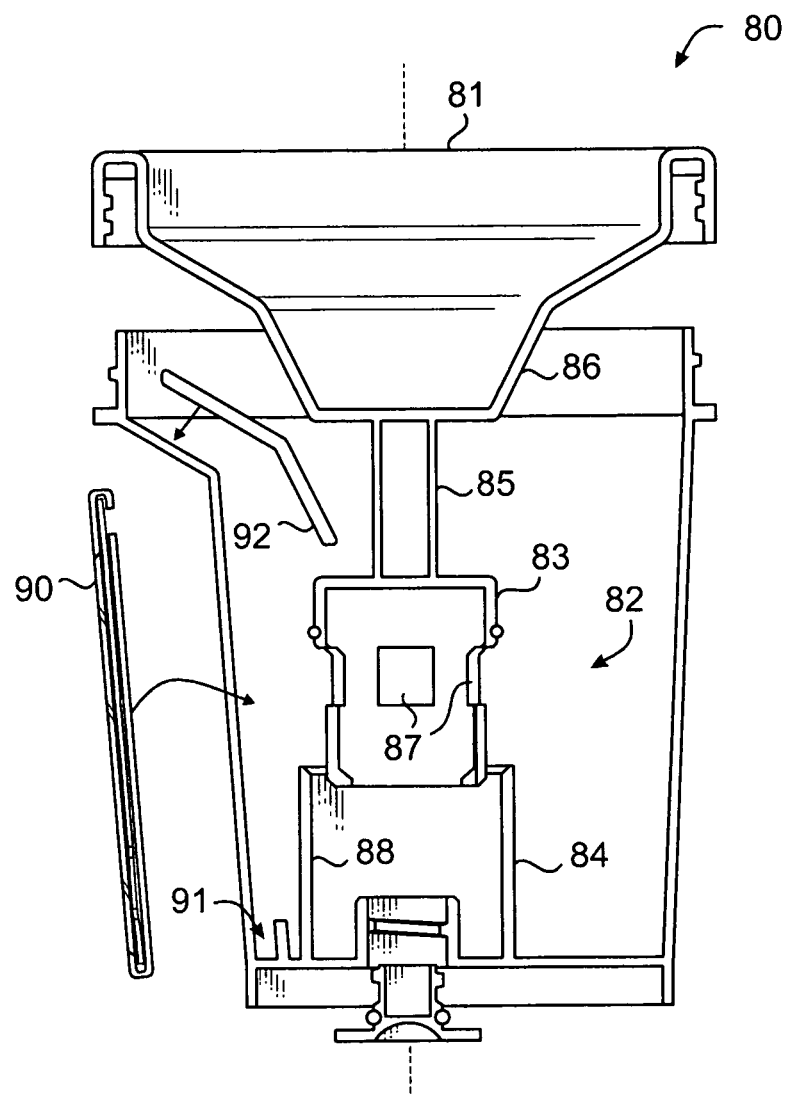
FIG. 8 is a diagrammatic exploded cross-sectional view of an alternate embodiment of the testing cup having an alternate confirmation sample preserving feature.

Referring now to FIG. 8, there is shown an alternate embodiment of a testing device 80 which is similar to the embodiment of FIG. 5. In this embodiment, the device has a tubular central enclosure 82 having two telescoping portions, namely, a well 84 and plunger cap 83 supported by a shank 85 projecting from the undersurface of the conical depression 86 of the cover 81. The plunger cap 83 has a series of lateral windows 87 to allow air to escape during the installation of the cover to trap of the small volume of fluid for later confirmatory testing. These windows are hermetically sealed by the wall 88 of the well once the cover has been installed. This embodiment also shows placement of a removable cartridge 90 within a retaining pocket 91 of the cup and being locked in place by a portion of the slash shield 92 contacting it when the shield is detachably secured to the cup.

While the preferred embodiments of the invention has been disclosed, modifications can be made and other embodiments may be devised without departing from the spirit of the invention and the scopes of the appended claims.

What is claimed is:

1. An assaying device for collecting a fluid sample, said device comprising:
   a container having an inner chamber, a peripheral wall, an opening defined by an upper edge of the peripheral wall, and a bottom wall;
   a cartridge located along the peripheral wall, the cartridge being shaped to hold at least one test strip and wherein the cartridge comprises an aperture in an upper section to allow fluid to contact the at least one test strip;
   a splash shield extending from the peripheral wall over said upper section of said cartridge, wherein the shield prevents the fluid sample from contacting the at least one test strip when the fluid sample is added to the container;
   a transparent window for viewing the at least one test strip; and,
   a lid for sealing the opening having a vertical rotation axis, the lid comprising a depression in a top surface of the lid, the depression forming a substantially conical void which projects downwardly into the container axially below said aperture when the lid seals the opening, thereby reducing the volume of said chamber an amount sufficient to raise a level of said fluid sample when said container is placed in an inverted orientation.

2. The device of claim 1, wherein said lid further comprises a substantially conical lower surface exposed to said inner chamber, whereby said substantially conical lower surface is continuously located adjacently spaced apart from said splash shield when the lid is being twisted into place.

3. The device of claim 2, wherein said device further comprises a pocket located along the peripheral wall shaped and dimensioned to allow for mounting said cartridge in an upright orientation or an inverted orientation with respect to said container.

4. The device of claim 1, which further comprises a tubular enclosure extending downwardly from an undersurface portion of said cover and having a bottom opening positioned to come in closing contact with a structure associated with said closed bottom when said cover is placed over said top.

5. The device of claim 4, which further comprises a resiliently compressible pad hermetically sealing said bottom opening against said structure associated with said closed bottom when said cover is placed over said top.

6. The device of claim 1, wherein said depression is axially symmetric about said vertical rotation axis of said lid.

7. The device of claim 1, wherein said depression is funnel-shaped.

8. The device of claim 1, wherein said depression comprises a central cavity closed at a upper region, and extending to contact a structure associated with said bottom wall when said lid is secured over said top.

\* \* \* \* \*